(12) United States Patent
Shadeck

(10) Patent No.: US 8,109,956 B2
(45) Date of Patent: *Feb. 7, 2012

(54) SYSTEMS AND METHODS FOR SURGICAL REMOVAL OF TISSUE

(75) Inventor: Louis M. Shadeck, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 573 days.

This patent is subject to a terminal disclaimer.

(21) Appl. No.: 12/044,644

(22) Filed: Mar. 7, 2008

(65) Prior Publication Data

US 2009/0228030 A1     Sep. 10, 2009

(51) Int. Cl.
*A61B 17/32*     (2006.01)

(52) U.S. Cl. ........................................... 606/167

(58) Field of Classification Search .......... 604/22, 604/118–119; 606/159, 167–171, 180
See application file for complete search history.

(56) References Cited

U.S. PATENT DOCUMENTS

| | | | |
|---|---|---|---|
| 5,037,386 A * | 8/1991 | Marcus et al. | 604/43 |
| 5,217,478 A | 6/1993 | Rexroth | |
| 5,712,543 A | 1/1998 | Sjostrom | |
| 6,017,354 A | 1/2000 | Culp et al. | |
| 6,037,724 A | 3/2000 | Buss et al. | |
| 6,090,123 A | 7/2000 | Culp et al. | |
| 6,500,169 B1 | 12/2002 | Deng | |
| 6,620,180 B1 * | 9/2003 | Bays et al. | 606/171 |
| 6,652,488 B1 | 11/2003 | Cover et al. | |

* cited by examiner

Primary Examiner — Ryan Severson
Assistant Examiner — Ashley Cronin
(74) Attorney, Agent, or Firm — Dicke, Billig & Czaja, PLLC

(57) ABSTRACT

A method for treating a body tissue comprises delivering a cutting mechanism of a surgical instrument into proximity to a target portion of the body tissue wherein the cutting mechanism includes a first member defining a lumen and a distal cutting tip. At least the first member is supported, via a coupler, by the handpiece. A fluid pathway extends from the distal cutting tip, through the lumen of the first member, and through an interior of the handpiece for fluid connection to a source of negative pressure. In one configuration, a coupler provides an internally-located aspiration control mechanism including a user interface port exteriorly exposed on the coupler and defining an aspiration control pathway extending from the user interface port to a proximal window of the inner member for communication with the lumen of the inner member. With the distal cutting tip placed into contact with the target portion, the treatment site is selectively aspirated by manipulating a position of a finger relative to the user interface port to manually effectuate an altering of a level of vacuum applied by the source of negative pressure at the distal cutting tip.

29 Claims, 11 Drawing Sheets

SYSTEMS AND METHODS FOR SURGICAL REMOVAL OF TISSUE

BACKGROUND

The present disclosure relates to treatment of body tissues. More particularly, it relates to surgical systems, instruments, and methods useful in reducing and/or removing tumorous tissues.

Removal or reduction of body tissues is performed for a variety of reasons and on many types of tissues. For example, an organ may be removed upon its failure. In some cases, a tumor and/or surrounding tumor must be eliminated. Tumors are commonly treated with chemotherapy, radiation, surgery, and other techniques. When surgery is the treatment of choice, a variety of surgical instruments, such as a cavitational ultrasonic surgical aspirator (CUSA) or a surgical laser knife, are commonly used.

Brain surgery is the treatment of choice for accessible brain tumors. While a CUSA may be used to treat many tissues other than brain tumors, brain surgery provides a useful example to highlight some of the difficulties arising in the surgical removal of delicate tissues. The goal of surgery is to remove as much tumor tissue as possible. Among other procedures, the most commonly performed surgery for removal of a brain tumor is a craniotomy. In general, the neurosurgeon makes an incision into the scalp, cranium, dura, meninges, and cortex to expose an area of brain over the tumor. Location and removal of the tumor then takes place.

The delicate tissues associated with the human brain anatomy give rise to several concerns when using a CUSA, laser knife, or other brain surgery instruments such as cold steel instruments, ultrasonic cutting devices, and bipolar radiofrequency plasma ablation systems. By way of reference, the brain is covered by three membranes or meninges that in turn are surrounded by the skull. The three layers of meninges are the dura mater (immediately beneath the skull), the arachnoid, and the pia mater. Spinal fluid flows in the space between the arachnoid and the pia mater membranes, known as the subarachnoid space. These meninges are thin and delicate, with the pia mater carrying or maintaining the many blood vessels associated with the brain. Due to the friable nature of especially the pia mater, neurosurgeons must exercise great care when attempting to surgically remove a brain tumor; unintended damage to the pia mater can diminish the primary blood supply to the brain. Unnecessary injury to other healthy structures, such as the arachnoid or brain tissue (e.g., cerebral cortex) as well as unnecessary injury to cranial nerves and arteries supplying the brain (and brain stem) also can lead to patient impairment. With this in mind, CUSA instruments deliver ultrasonic action to remove tissue and bone. The surgeon attempts to place the ultrasonic cutting tip against tissue to be destroyed. However, high frequency cutting may also occur and damage tissue surrounding the targeted tumor when touched by the instrument's shaft. Further, due to the relatively large size of the CUSA handpiece, it may be difficult to visually confirm placement of the ultrasonic shaft/tip. Similarly, use of a laser knife may give rise to unintended tissue damage due to local heat in and around the incision line.

In another example, when treating of tumors and/or lesions in the airway great care also must be taken with delicate tissues, such as the vocal cords or the esophagus. For instance, lesions or tumors must be removed while sparing the surrounding mucosa to avoid scarring the vocal cords. In another instance, an overly aggressive resection of tissue in the airway can lead to a fistula involving the esophagus, which in turn can lead to aspiration of food and fluid.

In light of the above, surgeons and others continue to face the many challenges presented during reduction or removal of tumors and/or lesions while attempting to minimize normal tissue damage.

DETAILED DESCRIPTION

Figure 1:
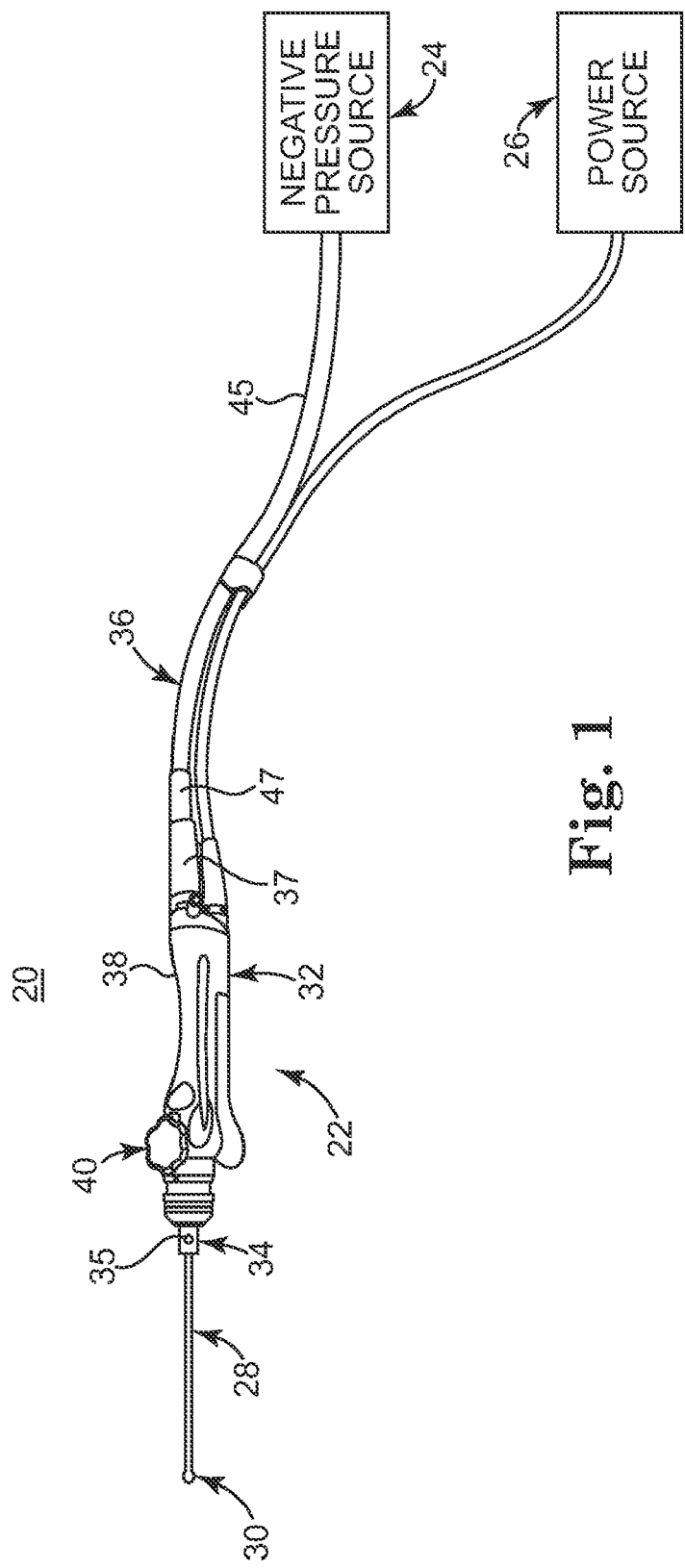
FIG. 1 is a schematic illustration of a system for surgically reducing or removing tissue in accordance with principles of the present disclosure.

Some aspects in accordance with principles of the present disclosure relate to a surgical system and method for surgically treating a tumor or other body tissue of a patient.

In one aspect, the system includes a surgical cutting instrument, a motor, and a source of negative pressure. The cutting instrument includes an inner member, an outer member, a handpiece, and an aspiration control mechanism. The inner member includes a distal cutting tip, whereas the outer member has a distal region forming a cutting window and an elevator tip distal the cutting window. The handpiece maintains the inner and outer members such that the inner member is rotatably received within the outer member, with the cutting tip being exteriorly exposed at the cutting window. Further, the cutting tip and the distal region combine to define a cutting implement. The motor is connected to the inner member for moving the inner member relative to the outer member, for example as part of a cutting operation.

In another aspect, the system includes a fluid pathway extending from the cutting implement through the handpiece to the source of negative pressure. In some configurations, the aspiration control mechanism is incorporated within the handpiece while in other configurations, the aspiration control mechanism is incorporated within a coupler configured to couple the inner and outer members to the handpiece. The aspiration control mechanism includes a control pathway integrated within an interior of the handpiece or of the coupler to define a segment of the fluid pathway. The aspiration control pathway includes a user interface port exposed on an exterior of the handpiece or the coupler and which is open to the ambient environment. The user interface port provides user control over a level of vacuum (supplied via the remainder of the fluid pathway and the negative pressure source) applied at the cutting implement. For example, by obstructing more or less of the user interface port, the level of vacuum applied at the cutting implement is increased or decreased, respectively. With some alternative constructions in accordance with principles of the present disclosure, the system is configured such that when the source of negative pressure is generating negative pressure and the user interface port is exteriorly unobstructed, a level of vacuum applied at the cutting implement is substantially zero.

Using this arrangement, a variety of body tissues and/or tumors can be treated. For the sake of illustration, treatment of a brain tumor is described. First, an opening is created through a skull of the patient to provide external access to a treatment site at which the brain tumor is located. The cutting implement is delivered through the opening to the treatment site. The elevator tip is inserted partially between the target tissue (e.g., the tumor) and the surrounding tissue of the treatment site, such as one or more of dura, arachnoid, pia, and cerebral cortex. The cutting tip is placed into contact with the tumor. The inner member is then moved relative to the outer member, thereby causing the cutting tip to cut tissue of the tumor. Finally, the treatment site is selectively aspirated to remove the cut or debrided tumor tissue. By using the elevator tip to at least partially isolate the tumor and selectively aspirating the treatment site, the likelihood of damaging the surrounding normal tissue is minimized. In some alternative aspects, methods of the present disclosure further include varying a level of vacuum (or aspiration rate) at the treatment site throughout the procedure, with the tumor being drawn into contact with the cutting tip via applied aspiration prior to a cutting operation.

Embodiments of the system also can be employed in removing brain tumors via other access pathways. For example, access to the brain may be obtained through the nose, palate, and oropharnyx to treat tumors such as pituitary tumors, clival cordomas, cholesterol granulomas, neuroesthesioblastomas, skull base meningiomas, and meningoceles. In another example, embodiments of the system are applied to treat to tumors via the lateral skull base, such as acoustic neuromas.

In other embodiments, tumors and/or lesions of the upper and lower airway are treated according to principles of the present disclosure. Non-limiting examples of these types of tumors and/or lesions include those generally occurring on the vocal cords, as well as recurrent respiratory papilloma, cysts, polyps, Reinke's edema or polypoid vocal corditis, benign tumors, and malignant tumors. In another non-limiting example, embodiments of the present disclosure are applicable to treating tumors and/or lesions in the bronchus.

The above system is highly useful in performing tumor surgery and other types of surgery. In tumor surgery, the system affords the neurosurgeon the ability to more precisely effectuate cutting only of the brain tumor, as well as to control aspiration applied to the treatment site.

These aspects, and other aspects, of the present disclosure are described and illustrated in association with FIGS. 1-9B.

A surgical system 20 in accordance with aspects of the present disclosure for reducing or removing body tissues is shown in FIG. 1. In just one example, system 20 can be used in debriding a brain tumor as part of brain surgery. The system 20 includes a surgical cutting instrument 22, a source of negative pressure 24, and a power source 26. Details on the various components are provided below. In general terms, however, the surgical instrument 22 includes a blade assembly 28 forming a cutting implement 30 (referenced generally), a handpiece 32, and an integrated aspiration control mechanism 34 (referenced generally). The source of negative pressure 24 is fluidly connected to the cutting implement 30 via a fluid pathway 36 extending up to and through a housing 38 of the handpiece 32. In one aspect, a proximal region of the handpiece 32 also includes an aspiration passage 37 that partially defines the fluid pathway 36 and which is fluidly connected to the negative pressure source 24 via tubing 47. Finally, the power source 26 is electrically connected to a motor (shown in FIG. 7B as motor 202) maintained by the handpiece 32.

During use in surgically reducing or removing a tumor, the cutting implement 30 is deployed to a treatment site, with the user manipulating the handpiece 32 to achieve a desired position of the cutting implement 30 relative to the brain tumor. The power source 26 energizes the motor to effectuate a tumor cutting operation at the cutting implement 30. Finally, the aspiration control mechanism 34 is manually operated by the user to selectively effectuate aspiration at the cutting implement 30 via a vacuum generated by the source of negative pressure 24. In some configurations, the aspiration control mechanism 34 includes a user interface port 35 which affords the user the ability to vary the rate or level of aspiration, as well as an aggressiveness of cutting at the cutting implement 30.

Figure 2:
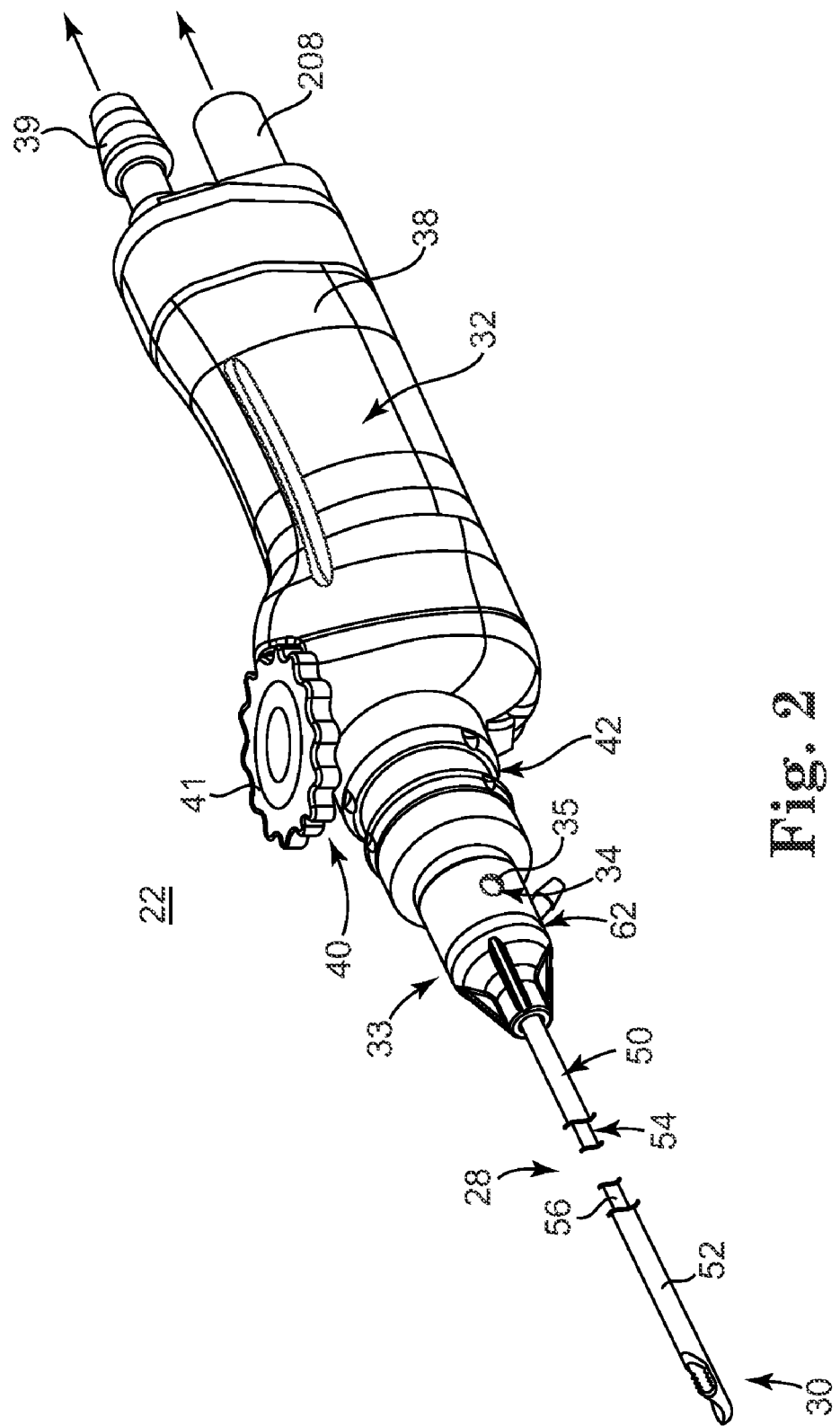
FIG. 2 is a perspective view of a surgical instrument useful with the system of FIG. 1.

With the above general construction of the system 20 in mind, features associated with the surgical instrument 22 in accordance with aspects of the present disclosure are shown in greater detail in FIG. 2. The surgical instrument 22 includes the blade assembly 28, the handpiece 32, and the aspiration control mechanism 34 as mentioned above.

In some configurations, surgical instrument 22 also includes a blade coupler 33 and/or a transition assembly 42. The blade coupler 33 is configured to couple the blade assembly 28 to handpiece 32. The blade coupler 33 includes the aspiration control mechanism 34 as well as variety of components facilitating control over several functions (e.g., cutting, rotation, etc.) of blade assembly 28. The transition assembly 42 is configured as a distal extension of the housing 38 of handpiece 32 and joins blade coupler 33 to handpiece 32. In some configurations, the transition assembly 42 is omitted with blade coupler 33 being directly connected to the housing 38 of the handpiece 32. While FIGS. 2-7B illustrate blade coupler 33 as positioned separate from (and distal to) housing 38, in yet other configurations, the functions of blade coupler 33 are incorporated within the housing 38 of handpiece 32.

In addition, in some embodiments, the surgical instrument 22 includes an optional control assembly 40 (referenced generally) configured to provide user control over a rotational position of a component of the blade assembly 28 as described below. In one aspect, control assembly 40 includes a rotatable wheel 41 configured to actuate a translation mechanism (not shown) within transition assembly 42 (or alternatively within housing 38), which in turn causes rotation of components of the blade assembly 28, as further described later in association with FIGS. 5-7B.

The blade assembly 28 can assume a variety of forms, and in some configurations includes an outer member assembly 50 having an outer member 52, and an inner member assembly 54 having an inner member 56. In general terms, the inner member 56 is rotatably disposed within the outer member 52, with other components of the assemblies 50, 54 defining portions of the blade coupler 33 to effectuate connection to the handpiece 32. Regardless, the outer and inner members 52, 56 extend distally from the handpiece 32, and combine to form the cutting implement 30 as described below. As a point of reference, while the blade assembly 28 is shown as including two of the members 52, 56, in other configurations, three or more co-axially assembled members can be provided. Further, the blade assembly 28, and in particular the members 52, 56, can have a linear or straight configuration as shown, or can alternately have a curved construction (such as by the inclusion of a curved member encompassing at least a portion of the outer member 52).

Figure 3A:
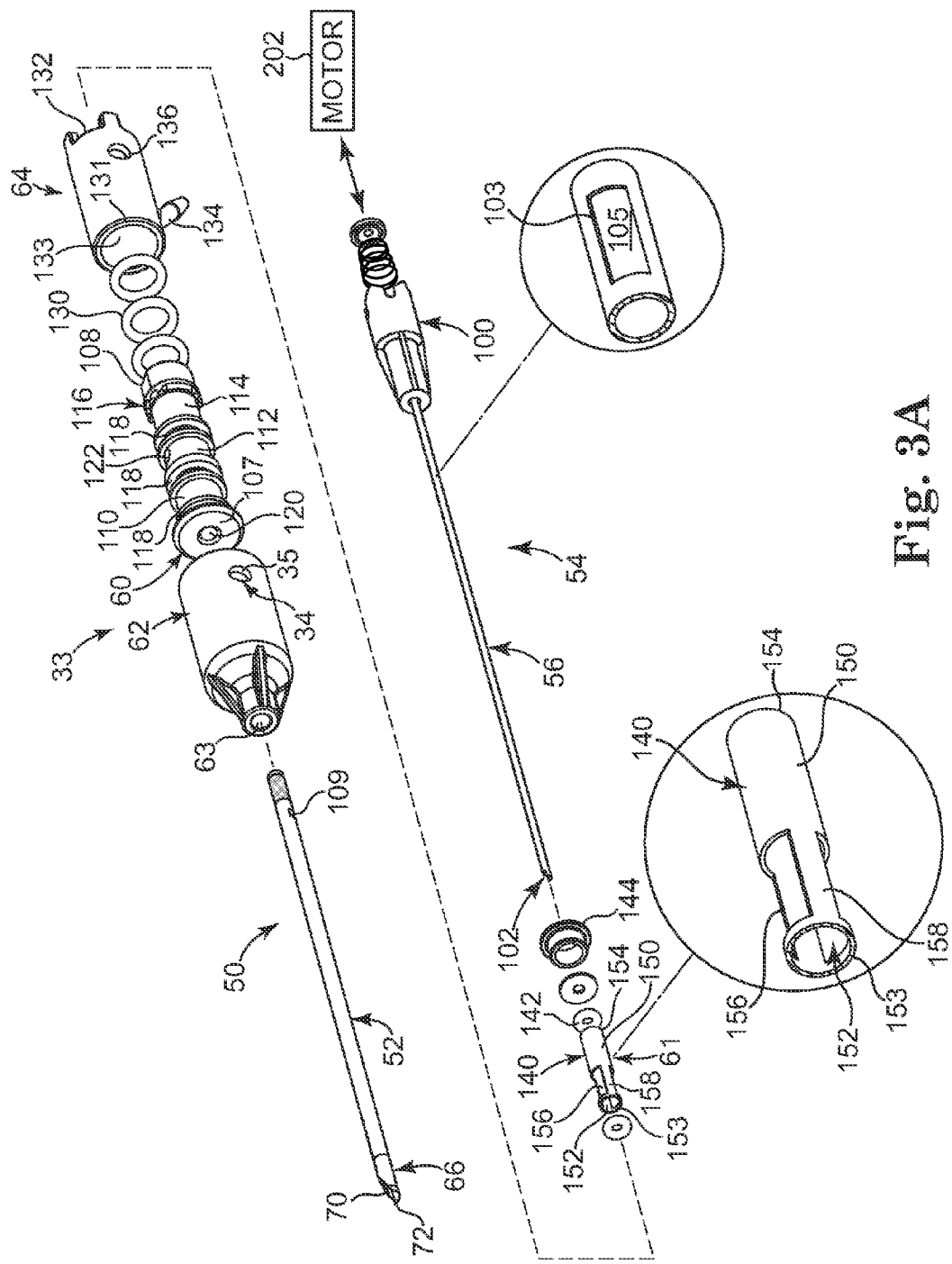
FIG. 3A is an exploded view of a blade assembly portion of the instrument of FIG. 2.
Figure 5:
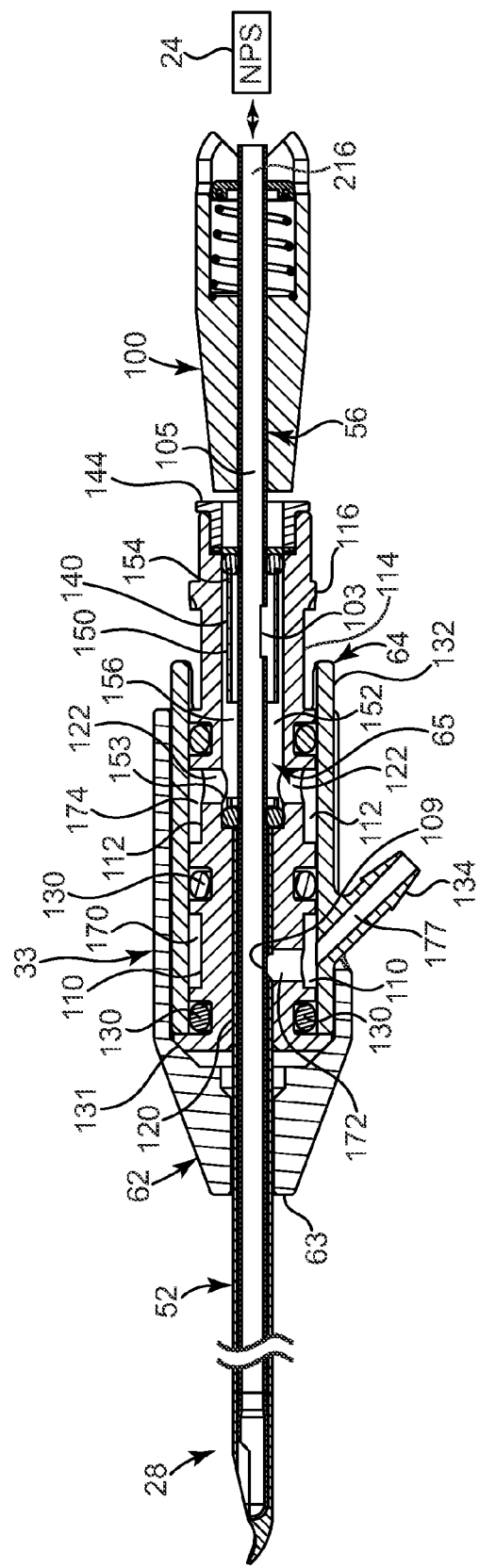
FIG. 5 is a cross-sectional view of the blade assembly and blade coupler of FIG. 3A upon final construction.
Figure 6:
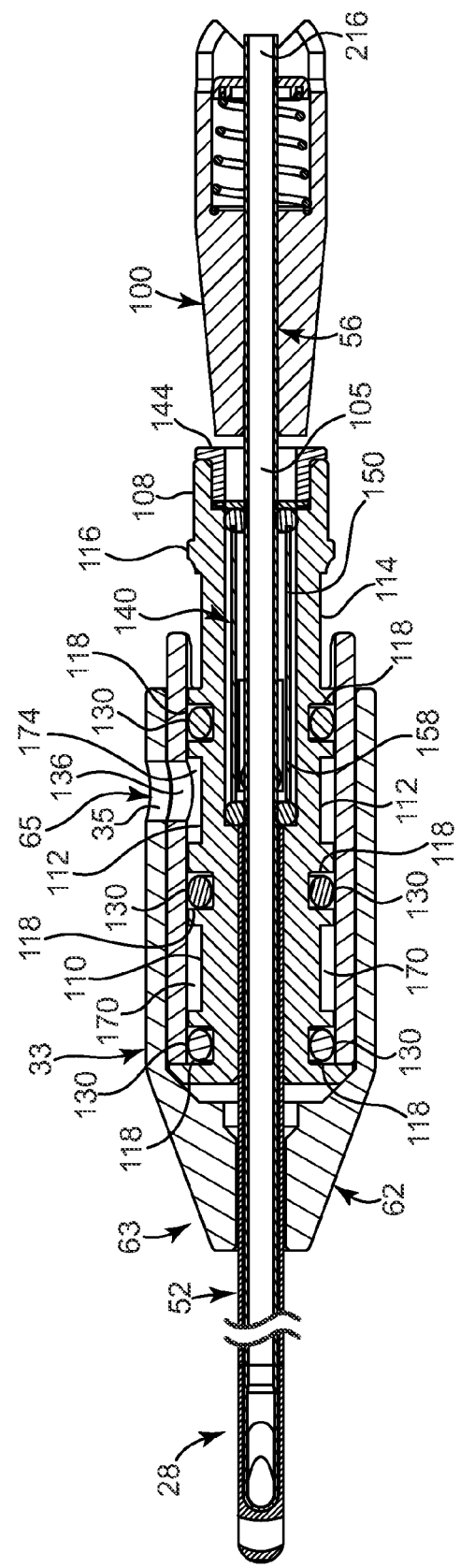
FIG. 6 is a cross-sectional view of the blade assembly and blade coupler of FIG. 3A upon final construction.

In one aspect, the aspiration control mechanism 34 also can assume a variety of forms, and in some configurations forms a part of blade coupler 33 with the user interface port 35 (also shown in FIG. 1) located distally of handpiece 32, as will be further described in association with FIGS. 3A and 5-6. In one aspect, aspiration control mechanism 34 defines an aspiration control pathway 65 (FIGS. 5-6) that forms a segment of fluid pathway 36 between cutting implement 30 and negative pressure source 24. The aspiration control mechanism 34 enables a user to control the amount of aspiration or vacuum at cutting implement 30 via selectively positioning their finger over the user interface port 35 while using the same hand to hold the handpiece 32 in position relative to the treatment site. In one aspect, user interface port 35 enables a comfortable placement of the control finger as it extends forward (and on a side of the handpiece 32) relative to the rest of their hand, which is gripping the handpiece 32.

As shown in FIG. 2, in some configurations, handpiece 32 also includes an aspiration port 39 and a wiring conduit 208. The aspiration port 39 is configured for connection to fluid pathway 36 and negative pressure source 24 (via port 37 and tubing 47 shown in FIG. 1). The wiring conduit 208 is configured to route wiring from a motor (shown as motor 202 in FIG. 7B) and/or other components from the housing 38 of handpiece 32 to power source 26.

With further reference to FIG. 3A, with some configurations, in addition to the outer member 52, the outer member assembly 50 includes an aspiration hub 60, an aspiration subassembly 61, a collet 62, an irrigation hub 64. The outer member 52 is secured to the aspiration hub 60, with the collet 62 facilitating attachment to the handpiece 32 as part of blade coupler 33. Further, where provided, the irrigation hub 64 facilitates delivery of an irrigation fluid to the outer member 52. Other constructions appropriate for assembling the outer member 52 to the handpiece 32 are also acceptable. Regardless, the outer member 52 is tubular in some embodiments, and forms a distal region 66. The distal region 66, in turn, forms in some configurations a cutting window 70 and an elevator tip 72 distal the cutting window 70.

Figure 4A:
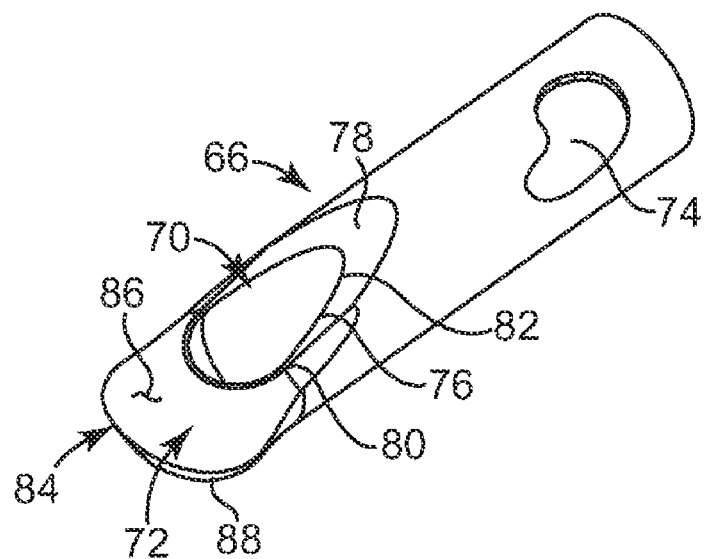
FIG. 4A is an enlarged, perspective view of a distal region of an outer tubular member of the assembly of FIG. 3A.

The distal region 66 can be an integrally formed component of the outer member 52, or can be separately formed and assembled to other components (e.g., the distal region 66 can be formed and then attached to an appropriately sized, rigid metal tube in completing the outer member 52). Regardless, one construction of the distal region 66 in accordance with principles of the present disclosure is shown in greater detail in FIG. 4A. As shown in FIG. 4A, the distal region 66 forms a lumen 74 that is otherwise open at the cutting window 70 (and continues proximally through at least a substantial portion of a remainder of the outer member 52 (FIG. 3A)). With this mind, the cutting window 70 is defined by a cutting window wall 76. A recessed portion 78 is formed in the distal region 66 about at least a proximal portion of the cutting window wall 76, such that the distal region 66 tapers in wall thickness along the recessed portion 78. As shown in FIG. 4A, in one embodiment the cutting window 70 can have a tear drop-like shape in longitudinal length, decreasing in lateral perimeter width from a distal segment 80 to a proximal segment 82.

The elevator tip 72 extends distal the cutting window 70, terminating at a sharpened or blade edge 84. In this regard, the elevator tip 72 is closed relative to the lumen 74. In one embodiment, the elevator tip 74 is defined by opposing, first and second surfaces 86, 88. The distal region 66 can assume a variety of forms, for example, including the forms described in U.S. patent application Ser. No. 11/938,625, filed Nov. 12, 2007, and entitled "Systems and Methods For Surgical Removal of Brain Tumors", the teachings of which are incorporated herein by reference.

The above construction of the elevator tip 72 (e.g., curved surfaces, increased width, and the blade edge 84) combine to provide the elevator tip 72 with a curette-like form. As described below, the elevator tip 72 is highly amenable for interfacing with the delicate tissues encountered during brain surgery (as well as other challenging treatment sites). The blade edge 84 promotes partial separation or isolation of tumor tissue from the brain and other normal tissue, with the curved surfaces 86, 88 assisting in isolating or separating the tumor from other tissue. In other configurations in accordance with the present disclosure, however, the elevator tip 72 can be eliminated. For example, the distal region 66 can terminate at the cutting window 70 that is otherwise axially and radially open to the lumen 74. Alternatively, the cutting window 70 can be formed in the distal region 66 as a side (or radial) window, with the outer member 52 having a relatively uniform outer diameter distal the cutting window 70.

Returning to FIG. 3A, the inner member assembly 54 includes the inner member 56, as well as an inner member hub 100. As described below, the inner member hub 100 maintains the inner member 56, and facilitates connection of the inner member assembly 54 (as part of blade coupler 33) to a motor 202 (represented schematically and also shown in FIG. 7B). Thus, the inner member hub 100 can assume a variety of forms. Regardless, with some constructions, the inner member 56 is tubular, forming a distal cutting tip 102. Moreover, in some configurations, the inner member 56 also forms a proximal aspiration window 103 exposing access to lumen 105. Proximal aspiration window 103 provides just part of aspiration control mechanism 34 and the fluid pathway 36 that enables fluid communication between the aperture 168 of distal cutting tip 102, user interface port 35, and negative pressure source 24, as further described later in association with FIGS. 5-6.

Figure 3B:
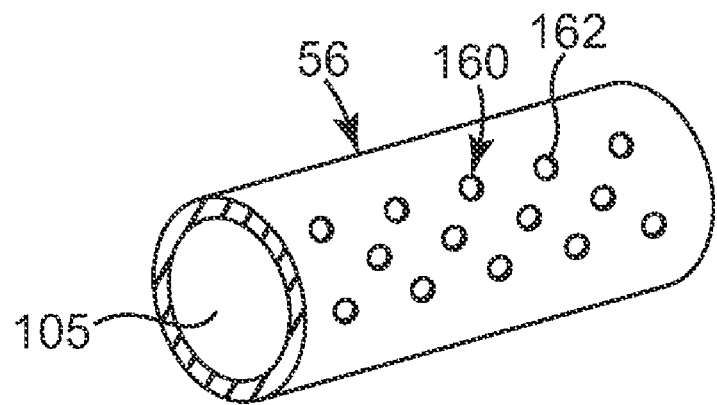
FIG. 3B is an enlarged, perspective view of a proximal region of an inner tubular member of the assembly of FIG. 3A.
Figure 3C:
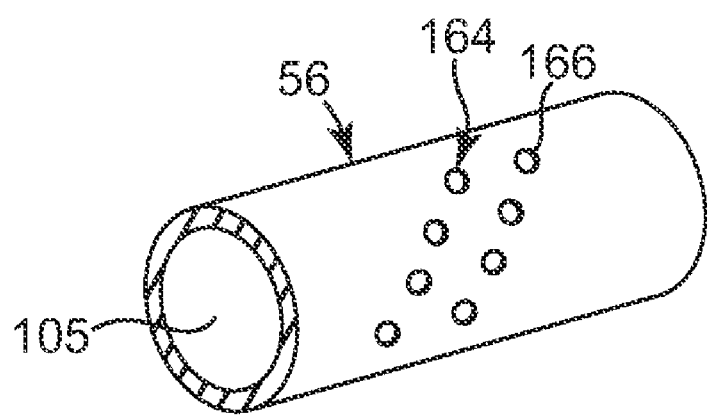
FIG. 3C is an enlarged, perspective view of a proximal region of an inner tubular member of the assembly of FIG. 3A.

In addition, while proximal aspiration window 103 is shown in FIG. 3A as having a generally rectangular shape, in some other configurations proximal aspiration window 103 can assume other forms such as a circular, elliptical, or polygon shape. Moreover, as illustrated in FIG. 3B, in some other configurations, proximal aspiration window 103 takes the form of an array 160 of holes 162 arranged in one or more rows along a wall of the inner member 56. Alternatively, as shown in FIG. 3C, proximal aspiration window 103 can take the form of an array 164 of holes 166 arranged in one or more spiral patterns about the wall of the inner member 56. In either case, holes 162, 166 provide a fluid communication path through a proximal portion of the inner member 56, with array 162 or 164 configured to be resistant to occlusion from tissue, fluids or other interferents.

Figure 4B:
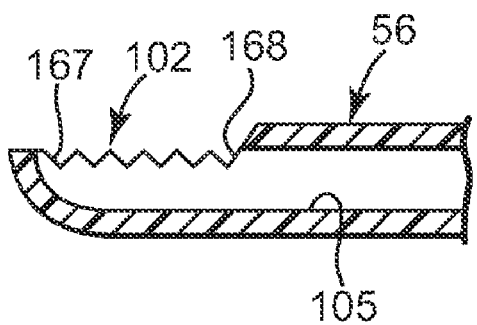
FIG. 4B is an enlarged, sectional view of a distal cutting window of an inner tubular member of the assembly of FIG. 3A.

In yet other configurations, and as shown in FIG. 4B, the cutting tip 102 can include a series of serrations or teeth 167. With this but one acceptable configuration, the teeth 167 are formed about an aperture 168 that is otherwise open to a lumen 105 defined by the inner member 56. As described below, the aperture 168 and the lumen 105 serve as an aspiration outlet of the fluid pathway 36 (FIG. 1) otherwise employed for aspirating a treatment site. Alternatively, the cutting tip 102 can assume other forms that may or may not include an aperture fluidly connected to a lumen. For example, the cutting tip 102 can be a closed burr.

In some configurations, fluid pathway 36 (FIG. 1) includes a segment defining an aspiration control pathway 65 (FIGS. 5-6) which establishes fluid communication between user interface port 35 and lumen 105 within inner member 56. In one aspect, as shown in FIG. 3A, aspiration control pathway 65 is defined by several components of blade coupler 33, including aspiration hub 60, aspiration subassembly 61, collet 62, irrigation hub 64, and portions of inner member 56.

While aspiration hub 60 can assume other forms, in one configuration as shown in FIG. 3A, aspiration hub 60 defines a generally tubular member sized and shaped for slidable insertion within irrigation hub 64 and collet 62, as later shown in FIGS. 5-6. Aspiration hub 60 includes a distal end 107, a proximal end 108, a distal lumen 120 for receiving outer member 52 (with inner member 56 arranged coaxially therein), and a proximal aspiration chamber 152 (shown in FIGS. 5-6). In some constructions and as shown in FIGS. 3A, 5-6, aspiration hub 60 includes a series of grooves 118 extending circumferentially about an outer surface of aspiration hub 60 with the respective grooves 118 being spaced apart from each other along a length of hub 60. An irrigation channel 110 is interposed between a distal one and an intermediate one of the respective grooves 118 while an aspiration channel 112 is interposed between the intermediate one and a proximal one of the respective grooves 118. In one aspect, aspiration channel 112 further defines a hole 122 to provide access to and fluid communication with a proximal aspiration chamber 152 (shown in FIGS. 5-6) formed within aspiration hub 60. In some configurations, adjacent proximal end 108, aspiration hub 60 also includes an extension portion 114 and a rotation-engaging mechanism 116 configured to be engaged by a portion of control assembly 40, as further described later in association with FIG. 7A. The rotation-engaging mechanism 116 of aspiration hub 60 is configured to translate rotational motion from the control assembly 40 to cause rotation of outer member 56.

Referring to FIG. 3A, seals 130 (e.g., O-rings) are provided for slidably fitting within the respective grooves 118, as further shown in FIGS. 5-6, to cause sealing of aspiration hub 60 relative to an inner surface of irrigation hub 64.

In some configurations, an aspiration subassembly 61 is provided and defines a portion of aspiration control pathway 65 extending within blade coupler 33. While aspiration subassembly 61 can assume a variety of forms, in some configurations, aspiration subassembly 61 comprises a generally tubular shaped sleeve 140 sized and shaped to fit within the proximal aspiration chamber 152 of aspiration hub 60. As shown in FIGS. 3A and 5-6, the sleeve 140 generally defines a lumen 152 extending between a distal end 153 and a proximal end 154. In some configurations, sleeve 140 further includes a proximal wall region 150 defining a generally continuous wall and a distal window region 158 defining at least one window 156 (two windows 156 are shown in FIG. 3A) exposing access to lumen 152.

In some configurations, aspiration subassembly 61 further includes one or more seals 142 and a plug 144 arranged to sealingly secure sleeve 140 within aspiration proximal chamber 152 of aspiration hub 60, as further illustrated in association FIGS. 5-6.

Referring again to FIGS. 3A and 5-6, while irrigation hub 64 can assume many forms, in some configurations, irrigation hub 64 includes a generally tubular shell defining a lumen 133 extending between a distal end 131 and a proximal end 132. In addition, irrigation hub 64 includes an irrigation port 134 and an aspiration aperture 136. The irrigation port 134 is configured for fluid connection to a fluid source (not shown). The aspiration aperture 136 is sized, shaped, and positioned for fluid communication with user interface port 35 of collet 62 and with hole 122 (within aspiration channel 112) of aspiration hub 60, as further illustrated in FIGS. 5-6.

Referring again to FIGS. 3A and 5-6, collet 62 of blade coupler 33 defines an outer shell sized and shaped to enclose and cover other components of blade coupler 33, including irrigation hub 64, aspiration hub 60, and aspiration subassembly 61 in their assembled form. In addition, collet 62 defines a lumen 63 sized to slidably receive and mount outer member 52. In general terms, collet 62 holds these components together, enabling each of these components to accomplish their respective functions to support operation of cutting implement 30 at a treatment site. In one aspect, with these components acting in a cooperative relationship as will be described further in association with FIGS. 5-7B, a user can control a level of vacuum at cutting implement 30 (FIG. 1) via selective placement of their finger relative to user interface port 35 of aspiration control mechanism 34 on collet 62. Because the aspiration control mechanism 34 is integrated within blade coupler 33 (as a distal extension of handpiece 32), a user can more effectively control vacuum pressure at cutting implement 30 without awkward positioning of their hand and fingers about the handpiece 32. Instead, arranging the user interface port 35 on side portion of collet 62 (distal to housing 38 of handpiece 32 as shown in FIG. 1) enables a more natural placement of a user's finger in a position distal to the rest of their hand which grasps the housing 38 of handpiece 32.

Figure 7A:
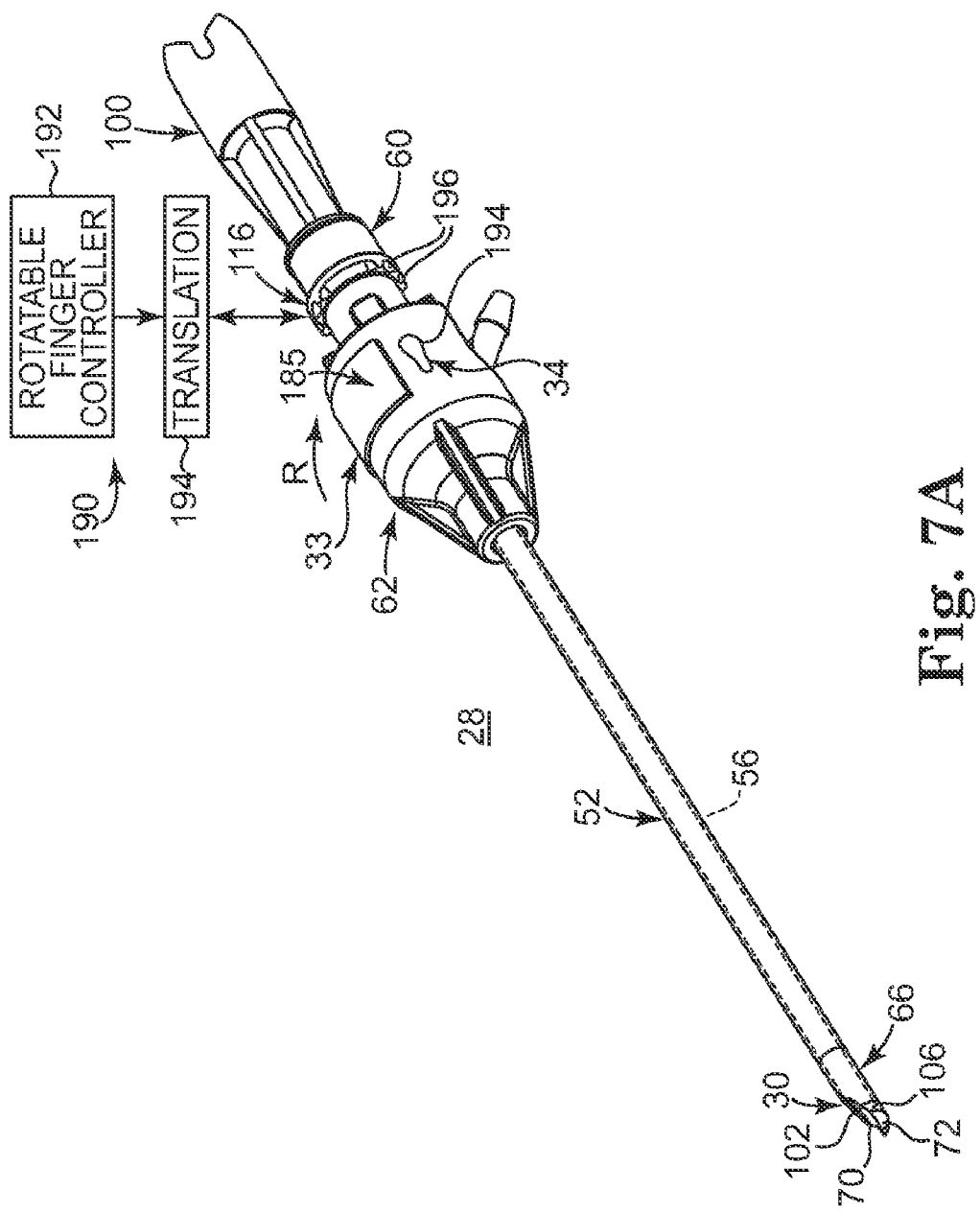
FIG. 7A is a perspective view of the blade assembly and blade coupler of FIG. 3A upon final construction.

Final construction of the blade assembly 28 and blade coupler 33, which include outer member assembly 50 and inner member assembly 52 is shown in FIGS. 5-7A, with FIGS. 5 and 6 providing cross-sectional views and FIG. 7A providing a perspective view. In general terms, the outer member 52 is secured via lumen 120 of the aspiration hub 60 (and therefore relative to lumen 63 of collet 62), which is in turn is received within the irrigation hub 64. The irrigation hub 64 comprises an inner shell that is slidably inserted and secured within the outer shell defined by collet 62. With these general relationships in mind, further details about the construction and interaction of these components will be described.

Referring to FIGS. 5-7A and as previously mentioned, seals 130 effectuate a fluid-tight seal between the irrigation hub 64 and the aspiration hub 60. With this construction, then, an irrigation liquid (not shown) is supplied through port 134 for delivery to the lumen 74 of the outer member 52 via a sealed gap 170 between the respective hubs 60, 64 (as defined by irrigation channel 110) and a bore 109 (FIGS. 3A and 5) formed in a proximal region of the outer member 52. In one aspect, the irrigation channel 110 extends circumferentially about an outer surface of aspiration hub 60 and generally transverse to a longitudinal axis of the aspiration hub 60. The assembled hubs 60, 64 are coaxially received with the collet 62, with the outer member 52 extending distal the collet 62 as shown. Other constructions capable of effectuating flow of irrigation liquid to the outer member 52 are also envisioned; in yet other configurations, the irrigation hub 64 (as well as any other irrigation component) can be eliminated.

Referring to FIGS. 5-6, the aspiration control mechanism 34 can assume a variety of forms, and in some embodiments, defines the aspiration control pathway 65 forming a segment of fluid pathway 36. In one aspect, the sealed, coaxial relationship of the aspiration hub 60 within the irrigation hub 64 also defines a gap 174 between seals 130 (within grooves 118) and the aspiration channel 112. However, unlike the irrigation channel 110, gap 174 is open to user interface port 35 via hole 136 of irrigation hub 64. Moreover, gap 174 is also open to proximal vacuum chamber 152 of hub 60 via hole 122 in the aspiration channel 112.

Accordingly, while not intending to be limited by directional terminology, the aspiration control pathway 65 begins, in one respect, with user interface port 35 of collet 62 (FIG. 6), extends through hole 136 of irrigation hub 64 (FIG. 6), into aspiration channel 174 (FIG. 5) of aspiration hub 60, through hole 122 from the gap 174 defined by aspiration channel 112 (FIG. 5) and down into proximal aspiration chamber 152 of aspiration hub 60 (FIG. 5), into window portion 156 of sleeve 140 (see FIGS. 5 and 3A) and through lumen 152 of sleeve 140 for passage into lumen 105 of inner member 56 via proximal aspiration window 103 (FIG. 5). Aspiration control pathway 65 joins to the rest of fluid pathway 36 via lumen 105 of inner member 56 which extends distally to aperture 168 at distal cutting tip 102 and which extends proximally through inner member hub 100 for passage through an interior of handpiece 32 for connection to negative pressure source 24. More details regarding the aspiration control pathway 65 in relation to the structure of the handpiece 32 are described and illustrated in association with FIG. 7B.

Accordingly, in general terms, the aspiration control pathway 65 establishes a segment of the fluid pathway 36 internally within blade coupler 33 (as an extension of handpiece 32) to establish fluid connection between the source of negative pressure 24 to the cutting implement 30 (via lumen 105 of inner member 50). More particularly, in some configurations, the aspiration control mechanism 34 (including its control pathway 65) is configured without an external structure on the housing 38 of handpiece 32, which could otherwise hinder a surgeon's handling of surgical instrument 22.

In one aspect, the introduction of proximal vacuum window 103 of inner member 50 enables an internal path for aspiration control mechanism 34, with proximal wall region 150 of sleeve 140 redirecting the fluid pathway distally into proximal aspiration chamber 152 (of aspiration hub 60) where distal window region 156 of sleeve 140 permits fluid communication between lumen 152 of sleeve 140 and proximal aspiration chamber 152. From this point, hole 122 in the aspiration channel 112 provides a generally direct fluid path from proximal aspiration chamber 152 to user interface port 35, since hole 122 is vertically aligned with hole 136 of irrigation hub 64 and with the hole in collet 62 that defines user interface port 35 on an exterior of blade coupler 33.

In other configurations, aspiration control pathway 65 not limited to particular arrangement shown in FIGS. 1-7B provided that a pathway extends from some portion of lumen 105 of inner member 50 (such as proximal vacuum window 103) internally within a distal portion of handpiece 32, a blade coupler 33, or similar structure to an exteriorly positioned user interface port (e.g., user interface port 35) accessible by the finger of a surgeon. Accordingly, in general terms, aspiration control pathway 65 as part of aspiration control mechanism 34 defines an exclusively internal fluid pathway bridging a user interface port (i.e., an exterior opening of a handpiece or as part of a distal extension of the handpiece) to a larger fluid pathway 36 extending between a cutting implement 30 and a source of negative pressure 24.

As noted above, with some embodiments, the fluid pathway 36 further extends through the lumen 105 of the inner member 56 (FIGS. 3A, 4B, and 5-6), and is open at the aperture 168 (FIG. 4B). However, with alternative configurations, the aspiration outlet at the cutting implement 30 can be provided in other forms that may or may not include the aperture 168 of the inner member 56 (e.g., aspiration can be provided via the outer member 52, via a separate tube provided with the blade assembly 28, etc.). Thus, the aspiration control mechanism 34 affords the user the ability to control a level of vacuum applied at the cutting implement 30.

As described below, control over the aspiration delivered at the cutting implement 30 (FIG. 1) is selectively effectuated by covering or uncovering the user interface port 35. In particular, a level or rate or vacuum delivered to or experienced at the aperture 168 (FIG. 4B), or other aspiration outlet configuration, will increase as the user interface port 35 (FIG. 1-3A) is increasingly covered, and vice-versa. With this in mind, the user interface port 35 has, in some configurations, a larger surface area as compared to the aspiration outlet provided at the cutting implement 30 through which suctioning is otherwise applied. For example, with some constructions, the aspiration outlet provided with the cutting implement 30 is the aperture 168 formed by the inner member 56 (FIG. 3). Commensurate with this description, then, a size of the user interface port 35 can be selected to be greater than a size of the aperture 168. As a result, when the user interface port 35 is entirely unobstructed, a vacuum level at the cutting implement 30 (i.e., at the aperture 168) is substantially zero in that the user interface port 35 provides a path of least resistance for negative pressure within the fluid pathway 36. Moreover, in some embodiments, the size of the user interface port 35 can be increased even more to be substantially larger than size of the aperture 168 to insure the elimination of suction at the cutting implement 30. Further, a user will readily "sense" vacuum or suction at the user interface port 35, and is thus provided with direct, tactile feedback as to a level of vacuum being applied at the cutting implement 30. Also the user interface port 35 affords essentially infinite control over the applied vacuum (between zero and maximum generated at the source of negative pressure 24) due to the absence of pre-established indexes or other stop mechanism along the aspiration control mechanism 34.

In some configurations, the user interface port 35 is embodied in a tear-drop shape (on an exterior of collet 62 of blade coupler 33) to yield user interface port 194, as shown in FIG. 7A. The variable cross-sectional area presented by the tear-drop shape enables more precise control over the level of aspiration during finger control by the surgeon.

In yet other configurations and as shown in FIG. 7A, collet 62 is provided with a rotatable cover 185 configured to selectively cover the user interface port 194 (or user interface port 35 having a circular shape). Thus, rotatable cover 185 enables the surgeon to block user interface port 194 for a period of time, in case it is desired to maintain closure of user interface port 194 (or user interface port 35) for an extended period of time. Later, the surgeon can simply rotate cover 185 away from user interface port 194 when it is desired to resume finger-controlled access to user interface port 194 (or a user interface 35 having a circular shape).

Final construction of the blade assembly 28 is further shown in FIG. 7A. As a point of reference, while the outer and inner members 52, 56 have been shown in as being linear, in other configurations, one or more bends or curves can be formed and/or additional tubular member(s) provided. The inner member 56 is received within the lumen 74 (FIGS. 5-6) of the outer member 52, and is attached to the inner member hub 100. The inner member hub 100, in turn, is positioned proximal the aspiration hub 60 and is rotatable relative thereto, such that rotation of the inner member hub 100 effectuates rotation of the inner member 56 relative to the outer member 52. Further, the cutting tip 102 of the inner member 56 is positioned at the cutting window 70 of the outer member 52. Thus, the cutting tip 102 is exteriorly exposed via the cutting window 70 for performing a cutting or debriding procedure. Finally, the distal region 66 of the outer member 52 (e.g., the cutting window 70 and the elevator tip 72) combine with the cutting tip 102 to form the cutting implement 30. Aspiration is effectuated at the cutting implement 30 via the aperture 168 provided with the inner member 56 (with the aperture 168 being exteriorly open through the cutting window 70). Alternatively, aspiration or suctioning at the cutting implement 30 can be provided by the outer member 52, a separate tubing carried by the cutting implement 30, etc. Similarly, irrigation is provided at the cutting implement via the outer member 52/cutting window 70, although in other embodiments, an additional irrigation supply tube (carried with or separate from the cutting implement 30) can be provided.

Returning to FIG. 2, the handpiece 32 and blade coupler 33 can assume a variety of forms that promote manipulation of the blade assembly 28/cutting implement 30 by a user, as well as powered movement of the inner member 56 relative to the outer member 52.

Figure 7B:
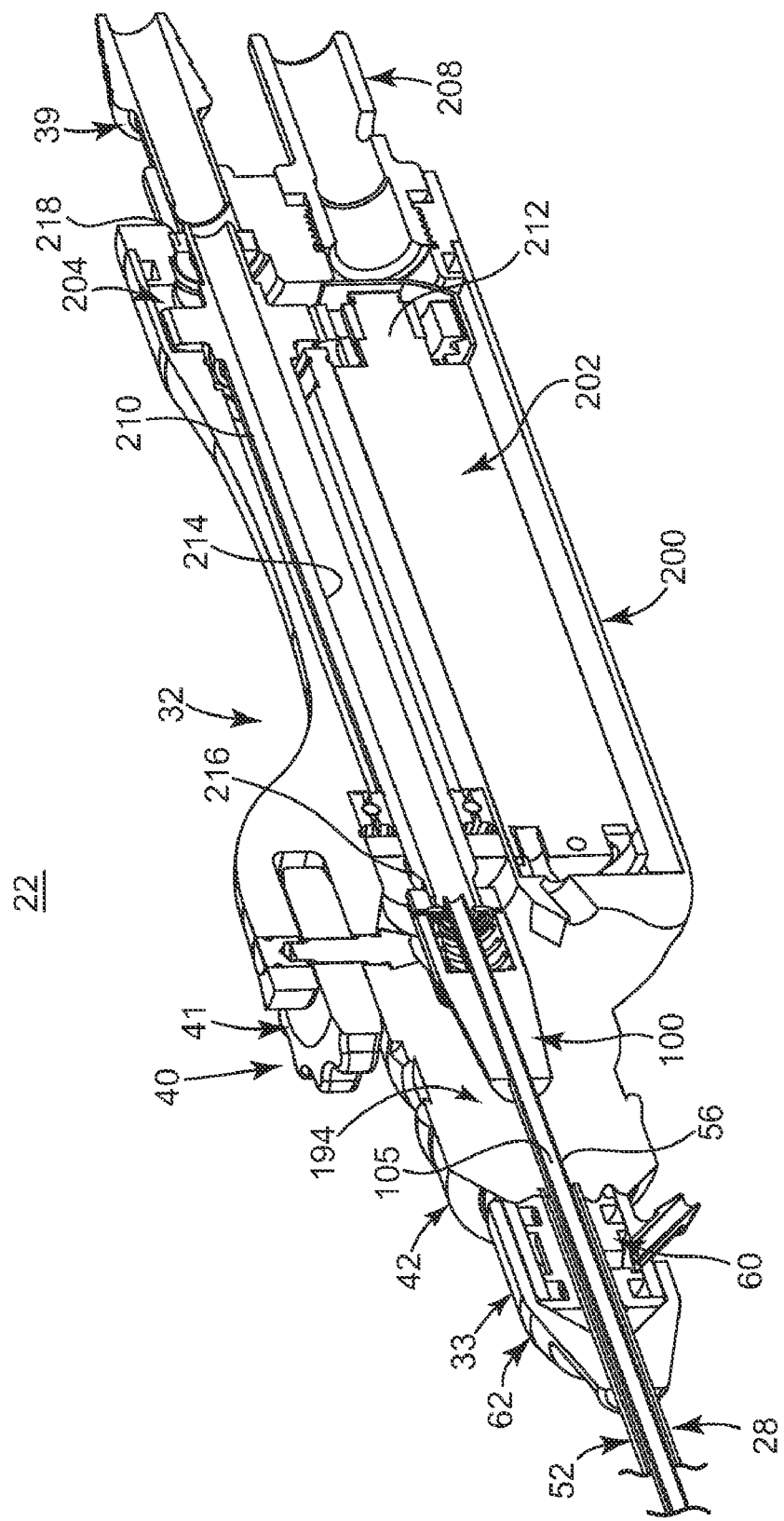
FIG. 7B is a cross-sectional view of a portion of the instrument upon final construction.

The optional control assembly 40 shown in FIG. 1 facilitates rotation of the outer member 52 relative to the inner member 56 as described below, and can assume a variety of forms. In some constructions and as shown in FIG. 7A, the control assembly 40 comprises an actuator 190 including a rotatable finger controller 192 and a translation mechanism 194, which is configured to translate motion of actuator rotatable finger controller 192 into rotation of outer member 52. The rotatable finger controller 192 can be akin to a wheel 41 as shown in FIG. 1, and is rotatably assembled to the housing 38 (or as represented by 200 in FIG. 7B). The translation mechanism 194 is configured to translate rotation of the rotatable finger controller 192 to the aspiration hub 60, and thus to the outer member 52. In this regard, translation mechanism 194 includes features adapted to interface with the rotation-engaging mechanism 116 of the aspiration hub 60. More particularly, and as best shown in FIG. 7A, in some constructions, the rotation-engaging mechanism 116 of the aspiration hub 60 is a series of circumferentially disposed indentations 196. In one arrangement, translation mechanism 194 includes features configured to interface with the indentations 196, akin to a ball and detent relationship. With this configuration, then, rotation of the rotatable finger controller 192 (e.g. wheel 41 in FIG. 1) is translated via translation mechanism 194 to the aspiration hub 60. Rotation of the aspiration hub 60, in turn, rotates the outer member 52. Because the aspiration hub 60 is not otherwise affixed to other components of the inner member assembly 54, rotation of the aspiration hub 60 results in rotation of the outer member 52 relative to the inner member 56. Importantly, rotation of the outer member 52 can be achieved by a user without overt movement of the housing 38 of handpiece 32 in FIG. 1 (or housing 200 as schematically represented in FIG. 7B). While grasping the housing 38 in his or her hand, the surgeon simply rotates the wheel 41 (represented schematically as rotatable finger controller 192 in FIG. 7A) with a finger (or thumb) of the same hand that is otherwise holding the housing 38 of the handpiece 32 shown in FIG. 1.

Returning to FIG. 2, the handpiece 32 can assume a variety of forms that promote manipulation of the blade assembly 28/cutting implement 30 by a user, as well as powered movement of the inner member 56 relative to the outer member 52. For example, FIG. 7B illustrates one construction of the handpiece 32 in accordance with the principles of the present disclosure. As a point of reference, for ease of illustration, certain proximal portions of the aspiration control mechanism 34 (FIG. 2) as they extend from blade coupler 33 through transition assembly 42 (such as the details of translation mechanism 194) are omitted from the view of FIG. 8. Further, the handpiece 32 is shown in FIG. 8 as being assembled to components of blade coupler 33, including portions of the blade assembly 28. With this in mind, the handpiece 32 includes a housing 200, the control assembly 40, a motor 202 (shown schematically in FIG. 7B), and a drive coupling 204. The motor 202 is secured within the housing 200, with the housing 200 forming a conduit 208 through which wiring (not shown) otherwise providing power to the motor 202 can extend. Further, the housing 200 preferably includes an output shaft 210 (which also defines a passage 214) and an aspiration port 39 for fluidly connecting the blade assembly 28 to the source of negative pressure 24 (FIG. 1) as described below. The drive coupling 204 mechanically connects the motor 202 to the inner member hub 100, and thus the inner member 56. To this end, a wide variety of constructions can be employed. With some configurations, however, the drive coupling 204 includes the output shaft 210 which is rotatably linked (e.g., geared) to a drive shaft 212 of the motor 132. The output shaft 210 can assume various forms, and with some constructions forms the passage 214 that, upon final assembly, fluidly connects the aspiration port 39 with a passageway 216 (see FIGS. 5-6) formed by the inner member hub 100 (and thus with the lumen 105 of the inner member 56 otherwise assembled to the passageway 216). Optional dynamic seals 218 can be included to better ensure a fluid-tight seal between the passage 214 and the aspiration port 39.

Figure 8A:
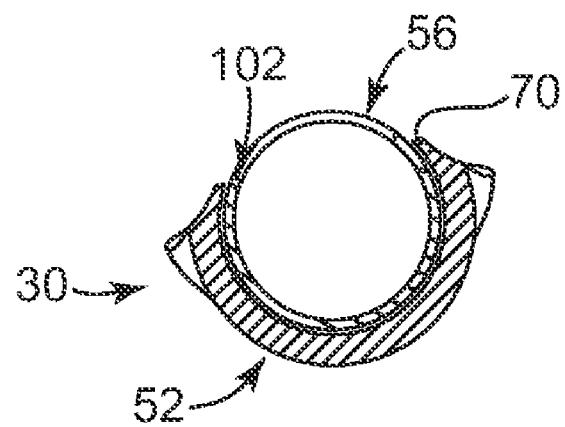
FIGS. 8A and 8B illustrate operation of a cutting implement portion of the instrument of FIG. 7.
Figure 8B:
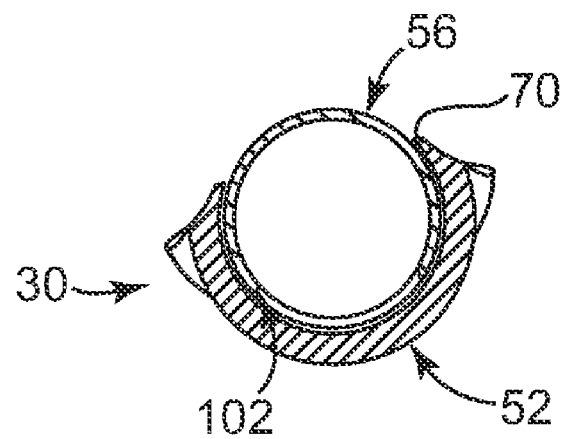

The control assembly 40 can assume a variety of other forms apart from the description provided above, for example as described in U.S. patent application Ser. No. 10/854,020 filed Sep. 22, 2004 and entitled "Surgical Cutting Instrument," the teachings of which are incorporated herein by reference. Conversely, with other constructions of the surgical instrument 22, the control assembly 40 is omitted (i.e., the outer member 52 cannot be independently rotated relative to the inner member 54). Where provided, however, rotation of the outer member 52 relative to the inner member 56 allows the user to selectively shield the cutting tip 102 from unintentionally contacting, and thus possibly damaging, delicate tissue of the brain and surrounding anatomy during a brain tumor debridement procedure. For example, as shown in FIG. 8A (in which only a portion of the outer member 52 is illustrated for purposes of clarity), a rotational position of the outer member 52 relative to the inner member 56 can be selected such that the cutting tip 102 is exteriorly exposed at the cutting window 70. With this orientation, the cutting tip 102 can contact and cut tissue adjacent the cutting implement 30. Conversely, the outer member 52 can be rotated relative to the inner member 56 such that the cutting tip 102 is within the outer member 52, as shown in FIG. 8B. With this arrangement, then, the outer member 52 prevents the cutting tip 102 from contacting, and possibly damaging, tissue. Along these same lines, the outer member 52 can be rotated to position or "face" the cutting window 70 at a desired location (e.g., a brain tumor) without movement of the handpiece 32 (FIG. 1) via the control assembly 40 (FIG. 1). That is to say, once the cutting implement 30 is delivered to a treatment site, the precise location at which cutting will occur (i.e., the cutting window 70) can be controlled by movement of the control assembly 40 (FIG. 1) (or as schematically represented by rotatable finger controller 192 in FIG. 7A). Accordingly, the surgeon will not be forced to contort his or her hand(s) to achieve a desired point of cutting/position of the cutting window 70.

Figure 9A:
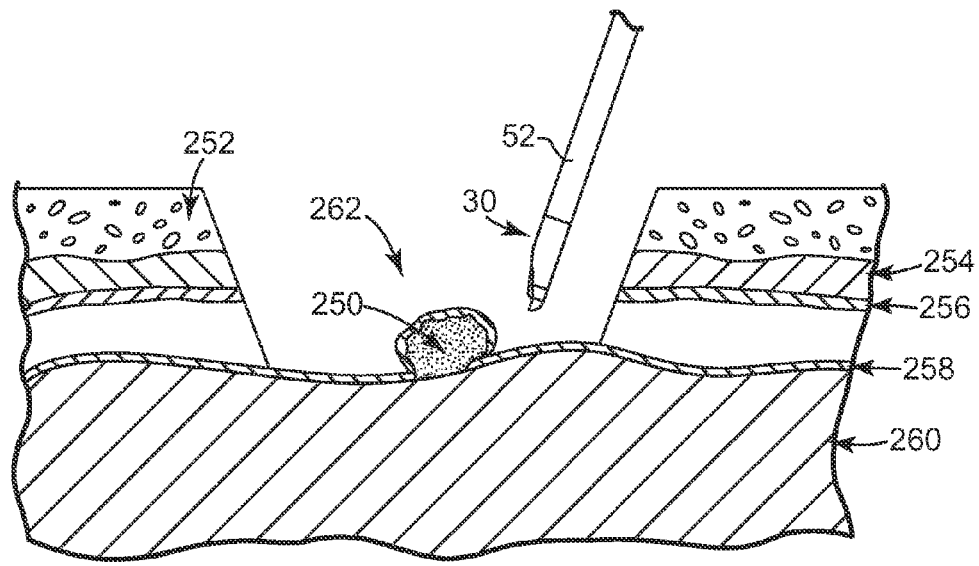
FIGS. 9A and 9B illustrate use of the system of FIG. 1 in surgically removing a brain tumor.

While the system 20 is generally useful in the surgical treatment (e.g., removal) of tumors, the system 20 is highly useful in the removal or reduction of brain tumors. In this regard, and with additional reference to FIG. 9A, treatment of a brain tumor 250 in accordance with aspects of the present disclosure includes forming an access opening in the patient's skull 252 (e.g., a conventional craniotomy). As a point of reference, FIG. 9A schematically illustrates other anatomy, including the dura 254, the arachnoid 256, the pia 258, and the cortex 260. The brain tumor 250 is shown as projecting from a natural anatomy of the cortex 260, exteriorly "covered" by the pia 258. With other procedures, the brain tumor 250 may be internal or embedded within the cortex (or other brain tissue) 260. Regardless, once a treatment site 262 at which the brain tumor 250 is located has been exposed, the system 20 is operated to remove at least some, preferably all, of the brain tumor 250.

The cutting implement 30 is deployed to the treatment site 262. During delivery of the cutting implement 30, the power supply 26 (FIG. 1) is inactive, such that the inner member 56 (FIG. 3A) does not move relative to the outer member 52 of blade assembly 28. Further, the source of negative pressure 24 (FIG. 1) may or may not be activated during initial placement of the cutting implement 30. That is to say, a negative pressure condition may or may not be established along the fluid pathway 36. Where the source of negative pressure 24 is activated, however, the user manually effectuates control over delivery of negative pressure to the cutting implement 30, such as by leaving the user interface port 35 (FIGS. 1-3A) associated with the aspiration control mechanism 34 uncovered. As described above, this arrangement causes virtually all of the negative pressure generated by the source of negative pressure 24 to be delivered to the user interface port 35, and thus not the aspiration outlet/aperture 168 of the cutting implement 30 in a manner that might otherwise negatively impact surrounding tissue of the treatment site 262.

Figure 9B:
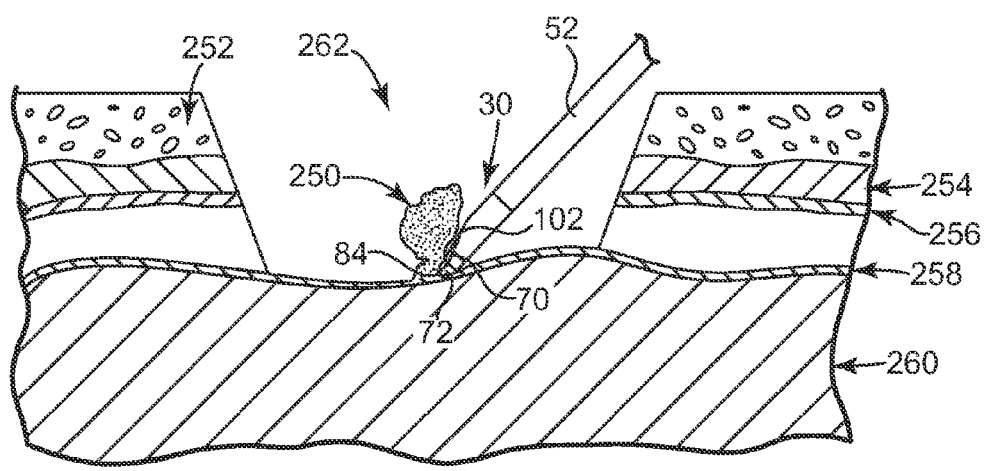

Once the cutting implement 30 is positioned adjacent the brain tumor 250, the surgeon manipulates the handpiece 32 so as to position the elevator tip 72 (where provided) partially between the brain tumor 250 and surrounding tissue of the treatment site 262. Where provided, the control assembly 40 (including wheel 41 as shown in FIG. 1) can be operated by the surgeon to rotate the elevator tip 72 to a desired spatial orientation relative to the treatment site 262 without overt twisting/contortion of the surgeon's hand(s). For example, as shown in FIG. 9B, the elevator tip 72 is positioned between the brain tumor 250 and a portion of the pia mater 258. Depending upon the particular location of the brain tumor 250, other non-tumor tissue of the brain anatomy may also or alternatively be implicated (e.g., the dura 254, arachnoid 256, cerebral cortex 260, etc.), with the elevator tip 72 partially isolating the brain tumor 250 from this tissue. Regardless, the elevator tip 72 at least partially separates or isolates the brain tumor 250 from the surrounding tissue with the blade edge 84 (FIG. 4A) possibly partially severing a portion of the brain tumor 250 away from the surrounding tissue. For example, the blade edge 84 can be manipulated to pierce the pia 258 at a relatively precise location in close proximity to the tumor 250. Further, by controlling (minimizing) aspiration at the cutting implement, unnecessary damage to the pia 258 (and other tissue) is avoided. The handpiece 32 can be further manipulated to cause the elevator tip 72 to pry the brain tumor 250 away from the surrounding tissue.

Once the elevator tip 72 is desirably positioned, the cutting tip 102 (referenced generally in FIG. 7A) is placed into contact with the brain tumor 250. For example, the outer member 52 is moved (e.g., rotated) such that the cutting window 70 "faces" the brain tumor 250. Further, with some techniques, the aspiration control mechanism 34 is manually operated to effectuate delivery of negative pressure to the cutting implement 30, thus drawing or suctioning the brain tumor 250 into contact with the cutting tip 102. For example, the surgeon can at least partially obstruct the user interface port 35 (FIGS. 1-3A), effectuating a more complete fluid connection between the source of negative pressure 24 and the aspiration aperture 168.

Due to the relatively compact and streamlined size and shape of the handpiece 32, the surgeon can readily, visually confirm desired placement and orientation of the cutting implement 30, and in particular the elevator tip 72 and the cutting window 70/cutting tip 102, relative to the brain tumor 250 and the surrounding tissue. Once the surgeon is satisfied with placement of the cutting implement 30, the power supply 26 is activated, thus causing the inner member 56 (FIG. 3) to move relative to the outer member 52. This action, in turn, causes the cutting tip 102 to move within the cutting window 70, cutting or debriding the contacted brain tumor 250. With some constructions, the motor 202 (FIG. 7B) operates to rotationally oscillate the cutting tip 102 relative to the cutting window 70. As part of this debriding procedure, the aspiration control mechanism 34 can be manually operated (e.g., movement of the surgeon's finger relative to the user interface port 35) to effectuate an increased vacuum level at the cutting implement 30, thus removing debrided brain tumor tissue from the treatment site 262.

During the debriding procedure, the surgeon can periodically confirm continued desired positioning of the cutting implement 30 relative to the brain tumor 250 and the surrounding tissue 256. Where, for example, it is determined that a differing point of cutting along the brain tumor 250 is desired, the outer member 52 can be rotated relative to the inner member 56 (FIG. 3), thereby altering a spatial position of the cutting window 70, and thus a point of contact of the cutting tip 102 with the brain tumor 250. For example, the wheel 41 of control assembly 40 shown in FIGS. 1-2 (and also represented by rotatable finger controller 192 shown in FIG. 7A) can be manipulated by the user's finger, causing a rotational position of the outer member 52 relative to the inner member 56 to change. Once again, and throughout the entire procedure, the level of vacuum or rate of aspiration can be manually changed at any time by the surgeon, for example by simply covering more or less of the user interface port 35 (FIGS. 1-7B).

The surgical systems and methods of the present disclosure provide a marked improvement over previous surgical techniques. The cutting implement, including the distal cutting tip and optional elevator tip, can safely remove selected target tissue, but not damage the surrounding tissues. Further, with selective variable aspiration, the target tissue can be isolated from the surrounding tissue for subsequent removal and more aggressive cutting. Moreover, by integrating an aspiration control mechanism within a blade coupler (or directly within a handpiece), the handpiece is not encumbered with extraneous structure an exterior of the handpiece, thereby facilitating nimble handling of the handpiece by the surgeon as well providing convenient finger control over aspiration. Further, the ability to rotate the outer member assists in protecting any delicate surrounding tissue (e.g., dura, arachnoid, pia, etc.)

such as when the cutting implement is used to treat brain tumors or to protect other delicate tissues (e.g., vocal cords, esophagus) when treating tumors or lesions in the airway.

Although the present disclosure has been described with reference to preferred embodiments, workers skilled in the art will recognize that changes can be made in form and detail without departing from the spirit and scope of the present disclosure.

What is claimed is:

1. A surgical method for treating a body tissue, the method comprising:
    obtaining access to a treatment site including the body tissue and delivering a cutting mechanism of a surgical instrument in proximity to a target portion of the body tissue, the cutting mechanism including a first member defining a lumen and a distal cutting tip, the distal cutting tip defining a first aperture;
    supporting the first member via a handpiece and interposing a coupler between the first member and the handpiece while containing a proximal portion of the first member substantially entirely within an interior of the handpiece;
    directly exposing an exterior surface of the coupler to the ambient environment;
    providing a fluid pathway that extends through the lumen of the first member from the distal cutting tip to a proximal end of the first member adjacent a proximal end of the handpiece at which the lumen of the first member is connected to a source of negative pressure, wherein the proximal portion of the fluid pathway is contained substantially entirely within the interior of the handpiece via the lumen of the first member;
    providing the first member with a proximal vacuum window intermediate to the distal cutting tip and the proximal end, with the proximal vacuum window defining a second aperture located within an interior of the coupler and in communication with the lumen, and further defining the fluid pathway from the proximal vacuum window of the first member, through an interior of the coupler, and to a third aperture exteriorly exposed on the coupler and in direct communication with the ambient environment;
    placing the distal cutting tip into contact with the target portion; and
    selectively aspirating the treatment site by selectively manipulating a position of a finger over the third aperture of the coupler to manually effectuate an altering of a level of vacuum applied by the source of negative pressure at the distal cutting tip.

2. The method of claim 1, wherein the proximal end of the handpiece includes an aspiration conduit in fluid communication with the proximal end of the lumen of the inner member and the system further includes tubing fluidly connecting the source of negative pressure with the aspiration conduit, and further wherein manually effectuating altering of a level of vacuum includes:
    covering more of the third aspiration aperture with the user's finger to increase a level of vacuum applied at the distal cutting tip; and
    covering less of the third aspiration aperture with the user's finger to decrease a level of vacuum applied at the distal cutting tip.

3. The method of claim 2, comprising defining an aspiration control pathway, as a portion of the fluid pathway that extends within the interior of the coupler, via:
    arranging a hub within the coupler;
    securing a proximal region of the second member within a distal lumen portion of the hub; and
    positioning the first member to extend through the distal lumen portion and through a chamber of the hub to position the proximal vacuum window of the first member to be proximal to the second member, to be within an interior of the chamber of the hub, and to be proximal to the third aspiration aperture,
    wherein the aspiration control pathway extends from the third aspiration aperture, through a wall of the hub that defines the chamber, through the interior of the chamber such that the aspiration control pathway extends into and through the lumen of the first member via the second aspiration aperture defined by the proximal vacuum window.

4. The method of claim 3 wherein arranging the hub within the coupler comprises:
    providing a first channel extending circumferentially about an exterior of the wall of the hub; and
    defining a hole through the wall of the hub, with the hole located within the first channel, such that the hole is in communication with the interior of the chamber to further define the aspiration control pathway to extend from the third aspiration aperture, through the first channel, through the hole in the wall of the hub, and into the interior of the chamber.

5. The method of claim 4, comprising:
    arranging a sleeve to extend within the interior of the chamber of the hub and to extend coaxially about the proximal vacuum window of the first member so that a proximal wall region of the sleeve is generally coextensive with the proximal vacuum window and so that a distal window region of the sleeve is distal to the proximal vacuum window, wherein the sleeve is separate from and independent of both the wall of the hub and the first member,
    wherein the aspiration control pathway at least partially extends from the interior of the chamber, into the distal window region of the sleeve, through a lumen defined by the proximal wall region of the sleeve, and into the lumen of the first member via the second aperture defined by the proximal vacuum window.

6. The method of claim 5, comprising:
    enclosing the hub within an outer shell of the coupler and interposing an inner shell between the hub and the outer shell, the outer shell defining the third aspiration aperture, wherein each of the outer shell and the inner shell are separate from and independent of the sleeve and wherein each of the outer shell and the inner shell are separate from and independent of the hub; and
    aligning the third aspiration aperture of the outer shell with a fourth aperture of the inner shell and the hole extending through the wall of the hub at the first channel to further define the aspiration control pathway.

7. The method of claim 5, wherein the proximal end of the sleeve terminates distal to the proximal end of the inner member.

8. The method of claim 3, wherein positioning the first member comprises:
    providing the first member with a proximal region that is proximal to the second aperture; and
    with the second aperture being positioned within the interior of the chamber of the hub, positioning the proximal region of the first member to be external to the chamber of the hub and to extend proximally beyond a proximal end of the hub.

9. The method of claim 1, wherein the cutting mechanism comprises a second member having a distal region forming a cutting window and an elevator tip, wherein the first member is rotatably received within the second member such that the distal cutting tip is exteriorly exposed at the cutting window, the distal cutting tip and the distal region combining to define the cutting mechanism, further wherein placing the distal cutting tip includes inserting the elevator tip between the target portion and a surrounding portion of the body tissue of the treatment site, which is further characterized by:

the source of negative pressure continuously operating to generate negative pressure; and the user manually effectuating a minimization of delivery of the negative pressure to the distal cutting tip.

10. The method of claim 1, wherein placing the cutting tip into contact with the target portion includes the user manually effectuating an increase in a level of vacuum applied by the source of negative pressure at the distal cutting tip to draw the target portion into contact with the distal cutting tip.

11. The method of claim 1, comprising:

selectively obstructing the third aspiration aperture via slidably moving a cover relative to the exterior of the coupler.

12. A surgical system for treating a body tissue, the system comprising:

a surgical cutting instrument including:

an inner member including a lumen extending between a distal cutting tip and a proximal end, with the inner member defining a proximal vacuum window at a location intermediate to the distal cutting tip and the proximal end, wherein the lumen is in fluid communication with the distal cutting tip, the proximal end, and the proximal vacuum window, and wherein the distal cutting tip defines a first aspiration aperture and the proximal vacuum window defines a second aspiration aperture;

an outer member having a distal region forming a cutting window;

a coupler maintaining the inner and outer members such that the inner member is rotatably received within the outer member, with the cutting tip being exposed at the cutting window, wherein the cutting tip and the distal region combine to define a cutting implement; and an aspiration control mechanism integrated within an interior of the coupler and defining an aspiration control pathway between the second aspiration aperture and a third aspiration aperture, the third aspiration aperture located on an exterior of the coupler and directly exposed to the ambient environment, wherein the lumen of the inner member is connectable to a source of negative pressure via the proximal end of the inner member, wherein the respective first, second and third apertures are in communication with each other and wherein the aspiration control mechanism is configured to enable user control over a level of vacuum applied at the distal cutting tip via selective positioning of a user's finger over the third aspiration aperture.

13. The system of claim 12 wherein the system is configured such that when the source of negative pressure is generating negative pressure and the third aspiration aperture is entirely unobstructed, a level of vacuum applied at distal cutting tip is substantially zero.

14. The system of claim 12 wherein the coupler comprises a hub secured to a proximal end of the outer member and enclosed within the coupler, wherein the hub includes:

a lumen through which the inner member extends;

a first fluid channel extending circumferentially about an exterior of the hub; and a chamber defined within the hub and extending proximally from the lumen of the hub, the chamber defining an interior sized, shaped, and positioned to enclose the second aspiration aperture of the inner member, wherein the second aspiration aperture of the inner member is proximal to the third aspiration aperture, and wherein a wall of the hub, at the location within the first channel, includes a hole in communication with the interior of the chamber and the third aspiration aperture is in communication with the hole within the first channel so that the aspiration control pathway extends from the third aspiration aperture, through the first channel, through the hole in the wall of the hub, through the interior of the chamber, and into the second aspiration aperture.

15. The system of claim 14 wherein the coupler comprises an outer shell and an inner shell coaxially disposed within the outer shell, the outer shell defining the third aspiration aperture and the inner shell defining a fourth aspiration aperture, wherein the third aspiration aperture and the fourth aspiration aperture define a portion of the aspiration control pathway and are in communication with the first channel, further wherein the hub is coaxially disposed within the inner shell.

16. The system of claim 15 wherein the coupler includes a sleeve supported within the chamber to be coaxially disposed relative to the inner member wherein the sleeve is interposed between, and in fluid communication with, the third aspiration aperture and the second aspiration aperture of the inner member, and wherein a proximal end of the sleeve terminates distal to the proximal end of the inner member.

17. The system of claim 16 wherein the proximal end of the outer member is positioned distal to the second aspiration aperture and the sleeve.

18. The system of claim 16 wherein the sleeve comprises a distal window region and a proximal wall region defining a lumen, further wherein the proximal wall region of the sleeve is generally coextensive with the second aspiration aperture of the inner member, wherein the distal window region of the sleeve is located distal the second aspiration aperture of the inner member, and wherein the distal window region of the sleeve is in fluid communication with both the second aspiration aperture of the inner member and the interior of the chamber.

19. The system of claim 12 wherein the second aspiration aperture comprises a single hole having a generally rectangular shape.

20. The system of claim 12 wherein the second aspiration aperture comprises an array of holes arranged in series.

21. The system of claim 12 wherein the second aspiration aperture comprises an array of holes arranged in a spiral pattern about a circumference of the inner member.

22. The system of claim 12 wherein the handpiece includes a movable cover disposed on an exterior of the handpiece configured to selectively close the third aspiration aperture.

23. The system of claim 12, wherein the third aspiration aperture is located distal to the second aperture defined by the proximal vacuum window and the third aspiration aperture is independent of, and separate from, a portion of the lumen of inner member that extends proximally from the proximal vacuum window for connection to a source of negative pressure.

24. The system of claim 12, and further comprising:

a handpiece containing a proximal portion of the inner member such that the proximal portion of the aspiration control pathway extends substantially entirely within the handpiece from the proximal vacuum window to the point of connection to the source of negative pressure.

25. A surgical system for deriding a brain tumor, the system comprising:
a surgical cutting implement including:
an inner member defining a lumen extending between a distal cutting tip and a proximal end with the inner member defining a proximal vacuum window located intermediate to the distal cutting tip and the proximal end, wherein the cutting tip defines a first aperture in communication with the lumen and the proximal vacuum window defines a second aperture in communication with the lumen;
an outer member including a distal region forming a cutting window,
wherein the cutting tip and the distal region combine to define a cutting implement with the cutting tip being exposed at the cutting window;
a handpiece supporting the inner member and the outer member;
a source of negative pressure fluidly connected to the cutting implement by a fluid pathway extending through the handpiece; and
means coupled to the handpiece for manually controlling a level of aspiration through the fluid pathway at the first aperture of the distal cutting tip and for maintaining the inner member to be rotatably received within the outer member, wherein the means for manually controlling is fluidly connected to the fluid pathway via the second aperture and includes a third aperture directly open to the ambient environment to provide finger-controlled management of a level of vacuum applied at the cutting implement based on the degree to which the user's finger obstructs the third aperture.

26. The system of claim 25, wherein the system is configured such that when the source of negative pressure is generating negative pressure and the third aperture is exteriorly unobstructed, a level of vacuum applied at the cutting implement is substantially zero.

27. The system of claim 26 wherein the handpiece includes a motor connected to the inner member for moving the inner member relative to the outer member.

28. The system of claim 25 wherein the means for manually controlling defines a coupler forming a distal extension of the handpiece and the coupler defines a further portion of the fluid pathway that is contained exclusively within an interior of the coupler.

29. The system of claim 28 wherein the coupler includes a hub defining a chamber that encloses the second aperture and the chamber is in fluid communication with the third aperture, wherein the hub also defines a lumen configured to secure a proximal end of the outer member, the lumen in communication with the chamber to allow extension of the inner member through the chamber.

* * * * *